United States Patent [19]

Richter et al.

[11] Patent Number: 5,265,466
[45] Date of Patent: Nov. 30, 1993

[54] ROD INSERTION METHOD AND FRICTION REDUCING DEVICE

[75] Inventors: David L. Richter; William T. Sweeney, both of Ponca City, Okla.

[73] Assignee: Conoco Inc., Ponca City, Okla.

[21] Appl. No.: 845,418

[22] Filed: Mar. 3, 1992

[51] Int. Cl.[5] ............................................. G01N 3/00
[52] U.S. Cl. ............................................. 73/85; 73/84; 175/325.1; 405/184
[58] Field of Search ............... 405/184, 231, 232, 250, 405/251, 252.1; 175/325.1; 73/84, 85; 384/29, 41, 280, 281

[56] References Cited

U.S. PATENT DOCUMENTS

| | | | |
|---|---|---|---|
| 420,951 | 2/1890 | Millhauser | 384/280 |
| 1,714,568 | 5/1929 | Pater | 384/281 |
| 2,481,931 | 9/1949 | Kester | 384/281 |
| 4,398,414 | 8/1983 | MacGregor | 73/84 |
| 4,649,741 | 3/1987 | Strom | 73/84 |

FOREIGN PATENT DOCUMENTS

| | | | |
|---|---|---|---|
| 538377 | 7/1922 | France | 384/281 |
| 1007263 | 10/1965 | United Kingdom | 73/84 |

Primary Examiner—Dennis L. Taylor
Assistant Examiner—Arlen L. Olsen

[57] ABSTRACT

The present invention provides a friction reducing device for an elongate member. The device comprises a friction reducing sleeve removably positionable on a first longitudinal segment of the elongate member. The present invention also provides a method of inserting an elongate assembly into the ground. The method comprises the step of incorporating the inventive friction reducing device in the elongate assembly.

37 Claims, 5 Drawing Sheets

ROD INSERTION METHOD AND FRICTION REDUCING DEVICE

FIELD OF THE INVENTION

In one aspect, the present invention relates to friction reducing devices for elongate members. In another aspect, the present invention relates to friction reducing devices for elongate assemblies. In yet another aspect, the present invention relates to methods of inserting elongate assemblies into the ground.

BACKGROUND OF THE INVENTION

Rods and rod strings are commonly driven into the ground for a variety of reasons. In conducting cone penetrometer tests, for example, rod strings are sometimes driven 300 or more feet into the ground.

Cone penetrometer systems are commonly used for analyzing subterranean materials and conditions and for developing stratigraphic maps. Recently, cone penetrometer systems have been used in addressing underground contamination problems. Through subsurface analysis, sample recovery, and mapping, cone penetrometer systems have been used to determine the existence and nature of underground contamination problems and to evaluate possible solutions.

A cone penetrometer system will typically utilize a long rod string having a sensing tool, a sampling tool, and/or some other type of tool positioned on the end thereof. The rod string is preferably driven, without drilling or turning, into the ground using a hydraulic ram. For convenience, the hydraulic ram is typically included on a cone penetrometer truck.

In conducting a cone penetrometer test, a relatively small diameter tubing string having a cone tip on the end thereof is typically driven into the ground first. The cone tip can be equipped with electronic sensors which take seismic readings and measure parameters such as: the frictional forces encountered by the rod string during the driving operation; pore water pressure; temperature; inclination; and resistivity. This data is processed and interpreted to obtain a complete stratigraphic map of the test site. Once the stratigraphic data is obtained, the small diameter rod string is typically pulled out of the ground.

Next, a rod string having a sample retrieving tool positioned on the end thereof can be driven into the ground. Sample retrieving tools are used to obtain soil and/or water samples from underground zones of particular interest.

Figure 1:
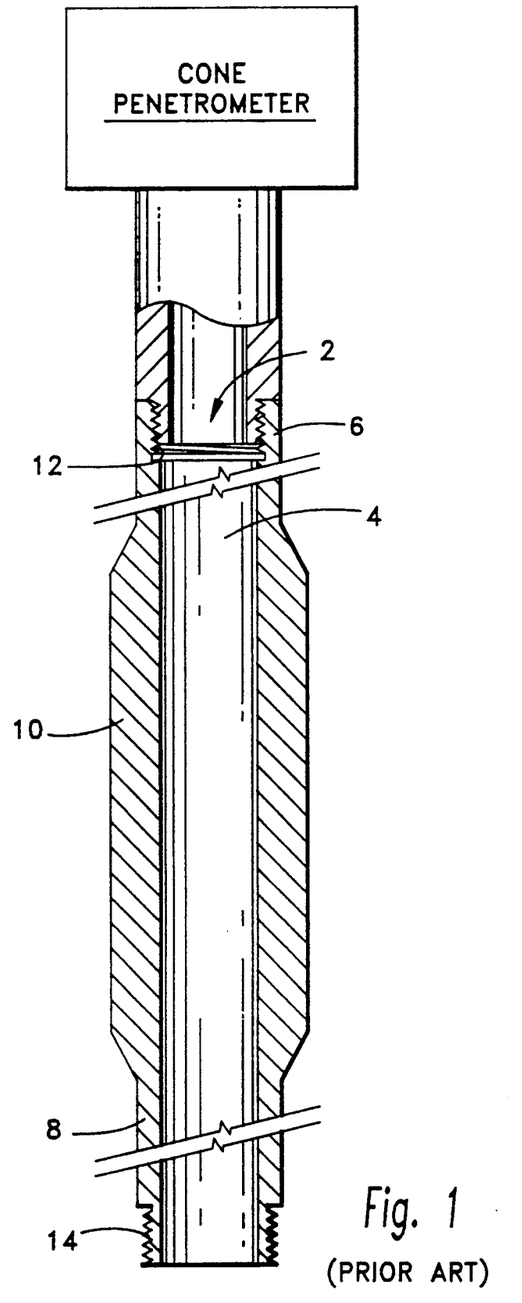
FIG. 1 provides an elevation side view of a friction reducing device 2 of the type heretofore used in the art.

In order to facilitate a rod string driving operation and to allow a rod string to be driven deeper into the ground, a rod string friction reducer can be used. A rod string friction reducer 2 of the type used heretofore is depicted in FIG. 1. Friction reducer 2 is an elongate member having a passageway 4 extending therethrough. Friction reducer 2 includes: a small diameter exterior portion 6 at one end thereof; a small diameter exterior portion 8 at the other end thereof; and a large diameter exterior portion 10 running between exterior portions 6 and 8. An internally threaded portion 12 is provided at one end of friction reducer 2 and an externally threaded portion 14 is provided at the other end of friction reducer 2. Threaded portions 12 and 14 are used for incorporating friction reducer 2 in a rod string. The outside diameters of small exterior portions 6 and 8 are preferably equivalent to the outside diameter of the rod string.

Friction reducer 2 is positioned near the end of a rod string. As the rod string is driven into the ground, friction reducer 2 enlarges the hole produced during the driving operation and thereby operates to reduce the amount of contact which occurs between the ground and the portion of the rod string extending above friction reducer 2. As a result, friction reducer 2 operates to reduce the overall frictional forces encountered by the rod string during the driving operation. Consequently, friction reducer 2 (a) facilitates the driving operation, (b) reduces the amount of stress to which the rod string is subjected during the driving operation, and (c) allows the rod string to be driven deeper into the ground.

In order to facilitate rod string driving operations, a cone penetrometer truck will typically have a guiding sleeve extending through the floor thereof. The guiding sleeve closely contacts and guides the rod string as the rod string is driven into the ground. Additionally, a rod decontamination system, for cleaning the rod string as it is pulled from the ground, will preferably be positioned adjacent the guiding sleeve. A rod decontamination system preferred for use in conjunction with the present invention is disclosed, for example, in U.S. patent application Ser. No. 07/591,347 filed Oct. 1, 1990, the entire disclosure of which is incorporated herein by reference. The decontamination system of U.S. patent application Ser. No. 07/591,347 includes a series of brushes and seals which closely contact the rod string. In order for the decontamination system of U.S. patent application Ser. No. 07/591,347 to be appropriately positioned on the rod string for use during the rod string pulling operation, the rod string is also conducted through the decontamination system as the rod string is driven into the ground.

When a cone penetrometer truck system of the type described above is used for driving a rod string into the ground, a friction reducer 2 of the type used heretofore cannot be connected to the end of the rod string until after the end of the rod string is conducted through the cone penetrometer system (i.e., through the truck's guiding sleeve and/or rod decontamination system). Large exterior portion 10 of friction reducer 2 is too large to travel through a close fitting guiding sleeve or through the close fitting seals of a rod decontamination system.

Since friction reducer 2 cannot be added to the end of the rod string until after the end of the rod string is conducted through the cone penetrometer truck's guiding sleeve and/or rod decontamination system, friction reducer 2, and any tool which is to be included in the rod string beneath friction reducer 2, must be added to the rod string after the end of the rod string is caused to protrude from the bottom of the cone penetrometer truck. In order to provide sufficient room beneath the cone penetrometer truck for connecting friction reducer 2 and the cone penetrometer tool to the end of the rod string, a hole must typically be dug beneath the cone penetrometer truck.

A need presently exists for an improved friction reducing device and method of installation which will eliminate the need to dig holes beneath cone penetrometer trucks. A need also exists for an improved friction reducing device and method of installation which will reduce the amount of rod string assembly and disassembly work which must be performed beneath cone penetrometer trucks.

Additionally, a need presently exists for an improved friction reducing device and method of installation which will allow friction reducers to be incorporated at desired positions along the entire length of a cone penetrometer rod string. As a penetrometer rod string having a single friction reducer 2 positioned on the end thereof is driven into the ground, the large exterior portion 10 of the friction reducer forms a hole having a diameter which is larger than the outside diameter of the upper portion of the rod string (i.e., the portion of the rod string extending above the friction reducer). Thus, as indicated hereinabove, the upper portion of the rod string is not restricted as the rod string is driven into the ground. However, if a portion of the hole collapses, the collapsed material will impinge upon the upper portion of the rod string and increase the amount of frictional drag encountered by the rod string during the driving operation. The amount of frictional drag created by the collapsed material could be reduced by including one or more additional friction reducers in the upper portion of the rod string. However, since the friction reducing device 2 used heretofore can only be added to the end of the penetrometer string after the end of the string is caused to protrude from the bottom of the cone penetrometer truck, additional friction reducers 2 cannot be incorporated in the upper portion of the penetrometer rod string.

A need also exists for an improved friction reducing device which (a) will allow a penetrometer tool to be positioned on the end of a penetrometer rod string before the end of the rod string is delivered through the bottom of the cone penetrometer truck and (b) will allow the penetrometer tool to be pulled, along with the remainder of the rod string, through a rod decontamination system and guiding sleeve. The ability to attach the penetrometer tool to the end of a rod string before the rod string is delivered through the bottom of a cone penetrometer truck would greatly reduce the amount of assembly work which must be performed beneath the truck. In like manner, the ability to subsequently pull the entire rod string, including the penetrometer tool positioned on the end thereof, through the truck's decontamination system and guiding sleeve would greatly reduce the amount of disassembly work which must be performed beneath the truck. Additionally, the ability to pull the penetrometer tool through the decontamination system along with the remainder of the rod string would greatly simplify the decontamination procedure by eliminating the need to disconnect and then separately decontaminate the penetrometer tool.

SUMMARY OF THE INVENTION

The present invention provides a friction reducing device for an elongate member. The inventive device comprises a friction reducing sleeve which is removably positionable on a first longitudinal segment of the elongate member.

The present invention also provides a method of inserting an elongate assembly into the ground. The inventive method comprises the step of incorporating a friction reducing device in the elongate assembly. The friction reducing device used in the inventive method comprises: an elongate member having a first, cylindrically-shaped, longitudinal segment; a friction reducing sleeve removably positioned on the first longitudinal segment; and a means for incorporating the elongate member in the elongate assembly.

The present invention resolves the problems discussed hereinabove. Using the inventive friction reducing device, a penetrometer tool can be conveniently positioned on the end of a penetrometer rod string before the end of the rod string is conducted through the bottom of a cone penetrometer truck (i.e., through said truck's guiding sleeve and/or rod decontamination system). Additionally, the inventive device allows the penetrometer tool to be pulled, along with the remainder of the rod string, through a rod decontamination system. Further, the only undertruck assembly and disassembly procedures required when using the inventive device involve, primarily, the addition and removal of the above-mentioned friction reducing sleeve. Consequently, the present invention substantially eliminates the need to dig a hole beneath the cone penetrometer truck and allows the incorporation of friction reducers at any desired locations along the entire length of a rod string.

Further objects, features, and advantages of the present invention will be readily apparent to those skilled in the art upon reference to the accompanying drawings and upon reading the following description of the preferred embodiments.

DESCRIPTION OF THE PREFERRED EMBODIMENTS

Figure 2:
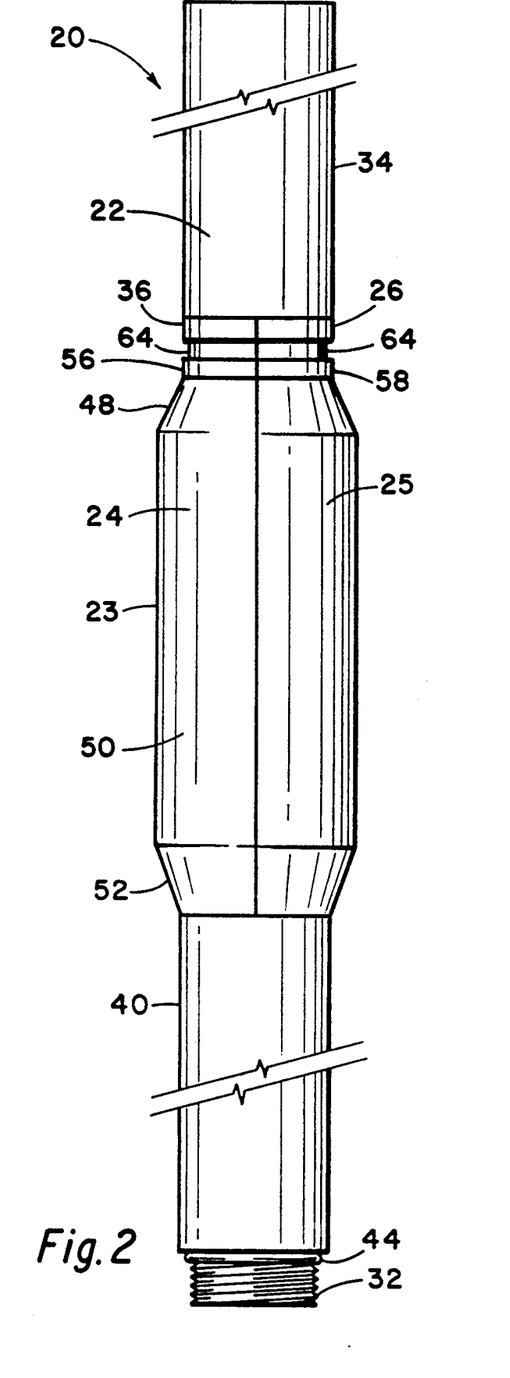
FIG. 2 provides an elevational side view of an embodiment of the device 20 of the present invention.
Figure 3:
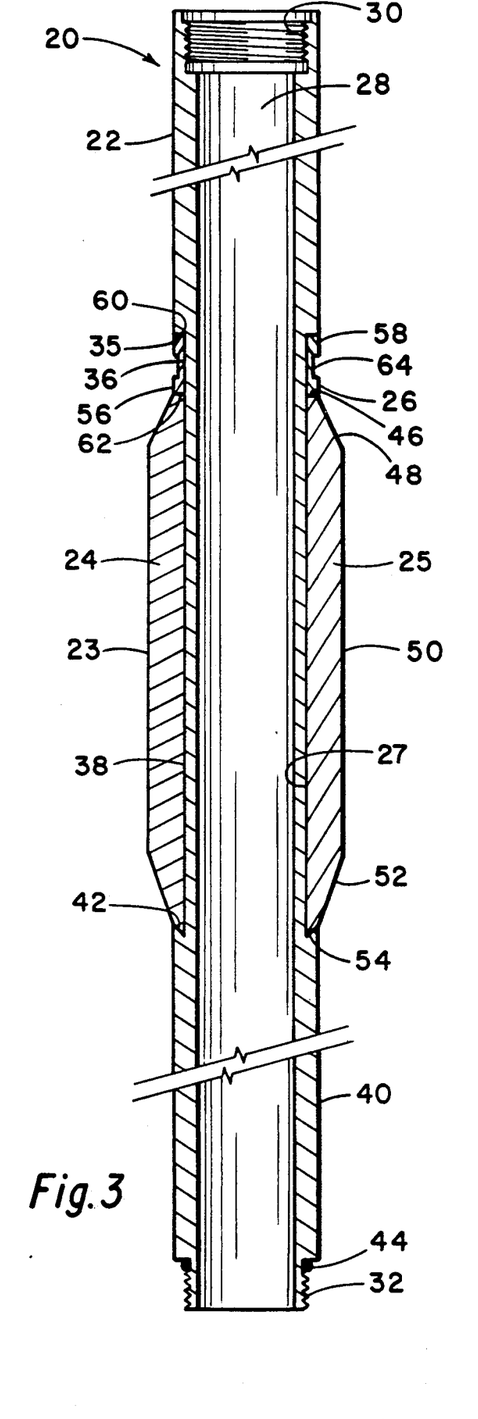
FIG. 3 provides a cutaway elevational side view of inventive device 20.
Figure 4:
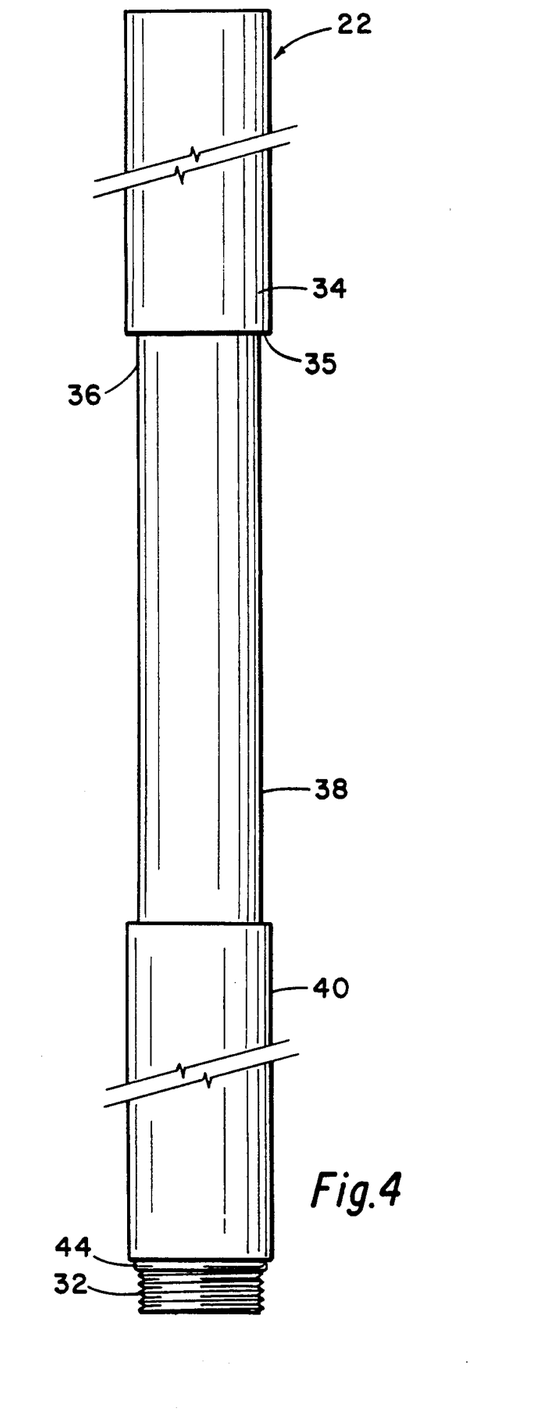
FIG. 4 provides an elevational side view of elongate member 22 of inventive device 20.
Figure 5:
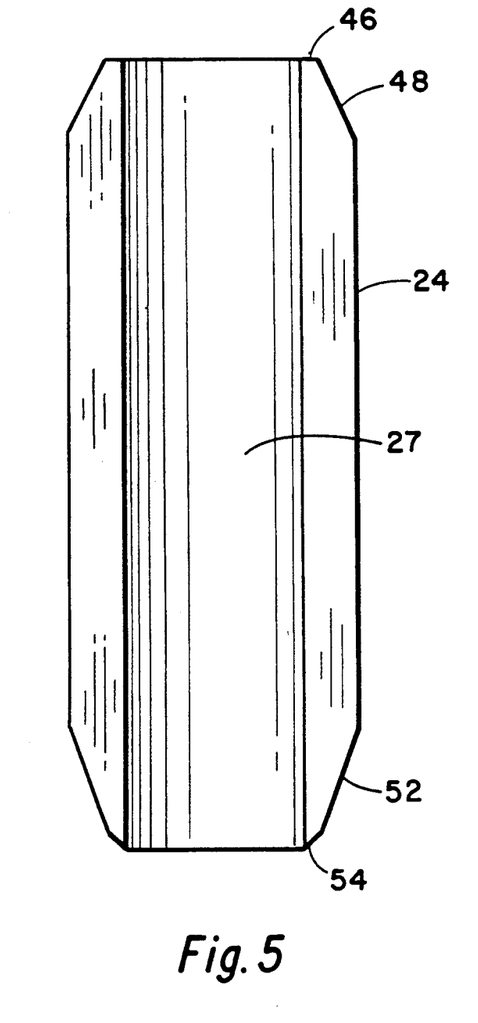
FIG. 5 provides an elevational side view of sleeve member 24 of inventive device 20.
Figure 6:
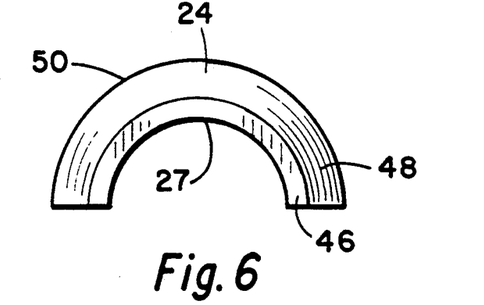
FIG. 6 provides a top view of sleeve member 24.
Figure 7:
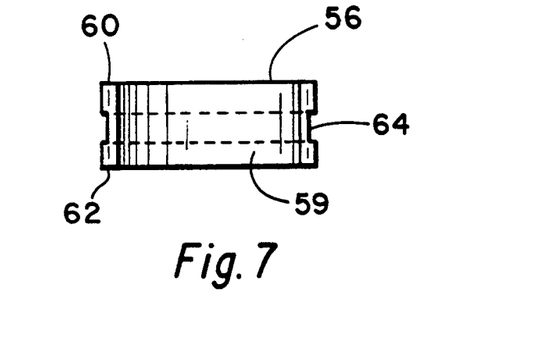
FIG. 7 provides a side view of retaining member 56 of inventive device 20.
Figure 8:
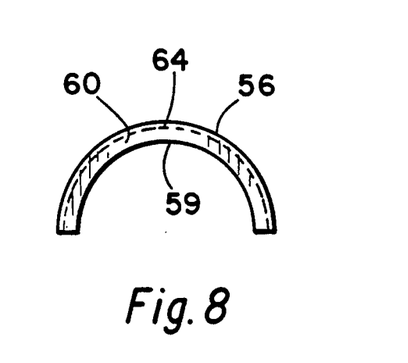
FIG. 8 provides a top view of retaining member 56.

A preferred embodiment of the inventive device 20 is depicted in FIGS. 2 and 3. Inventive device 20 comprises: an elongate member 22, a friction reducing sleeve 23, and a retaining means 26.

Elongate member 22 is a tubular member having a passageway 28 extending therethrough. Elongate member 22 has an internally threaded portion 30 at one end thereof for connecting elongate member 22 to the end of a rod string (e.g., to the end of a small diameter tubing string or a similar elongate assembly). Elongate member 22 has an externally threaded portion 32 at the other end thereof for connecting a penetrometer tool (e.g., a cone tip) or other member to elongate member 22. Elongate member 22 further includes: a first cylindrical exterior portion 34 extending from the internally threaded end of elongate member 22; a second cylindrical exterior portion 36 adjacent exterior portion 34 for receiving retaining means 26, portion 36 having a smaller outside diameter than portion 34; a third exterior portion 38 adjacent exterior portion 36 for receiving friction reducing sleeve 23, portion 38 having an outside diameter equivalent to the outside diameter of portion 36; and a fourth exterior portion 40 extending from exterior portion 38 to the male threaded end of elongate member 22, portion 40 having an outside diameter equivalent to the outside diameter of portion 34. Exterior portion 34 and exterior portion 40 each preferably have an outside diameter which is equivalent to the outside diameter of the rod string to which device 20 is connected. As shown in FIG. 3, the transition between third exterior portion 38 and fourth exterior portion 40 defines a V-shaped groove 42 for receiving one end of friction reducing sleeve 23.

An O-ring 44 is provided at the base of externally threaded portion 32 of elongate member 22 for sealing the connection between elongate member 22 and the penetrometer tool or other member connected to portion 32.

Friction reducing sleeve 23 is removably positionable around third exterior portion 38 of elongate member 22. When positioned on elongate member 22, friction reducing sleeve 23 preferably extends around substantially the entire circumference of exterior portion 38. Friction reducing sleeve 23 preferably comprises two substantially identical sleeve members 24 and 25. Each of sleeve members 24 and 25 extends over not more than about one-half of the circumference of third exterior portion 38. Each sleeve member 24, 25 has a semi-cylindrical interior surface 27 which is positionable against third exterior portion 38. Each sleeve member 24, 25 further includes: a flat end 46 for abutting retaining means 26; a first tapered exterior portion 48 extending from flat end 46; a semi-cylindrical exterior portion 50 having one end adjacent tapered exterior portion 48; a second tapered exterior portion 52 extending from the other end of semi-cylindrical exterior portion 50; and a V-shaped end 54 adjacent second exterior portion 52, end 54 being receivable in V-shaped groove 42. When assembled on third exterior portion 38 of elongate member 22, the cylindrical exterior portion of friction reducing sleeve 23 formed by semi-cylindrical exterior portions 50 has an outside diameter greater than the outside diameter of cylindrical exterior portions 34 and 40.

Although the friction reducing sleeve 23 depicted in FIGS. 2 and 3 includes only two sleeve members 24 and 25, sleeve 23 could alternatively be comprised of three or more sleeve members. However, regardless of the number of sleeve members used to form the friction reducing sleeve, none of the sleeve members should extend over more than one-half of the circumference of third exterior portion 38. As is apparent, if none of the sleeve members extends over more than one-half of the circumference of portion 38, then all of the sleeve members can be easily placed on, and removed from, portion 38.

Retaining means 26 is removably positionable around second exterior portion 36 of elongate member 22. When positioned on elongate member 22, retaining means 26 preferably extends around substantially the entire circumference of exterior portion 36. Retaining means 26 preferably comprises two substantially identical semi-cylindrical retaining members 56 and 58. Each semi-cylindrical retaining member extends over not more than about one-half of the circumference of second exterior portion 36. Each retaining member has a semi-cylindrical interior surface 59 which is positionable against second exterior portion 36. Retaining members 56 and 58 further include: flat ends 60 for abutting the shoulder 35 of elongate member 22 formed by the transition from first cylindrical exterior portion 34 to second cylindrical exterior portion 36; flat ends 62 for abutting the flat ends 46 of sleeve members 24 and 25; and grooves 64, formed in the exterior surfaces of retaining members 56 and 58, for receiving a nylon tie, a wire, or similar tying means (not shown). The tying means serves to hold retaining members 56 and 58 and friction reducing sleeve members 24 and 25 in position on elongate member 22 when device 20 is suspended above the ground and while device 20 is being driven into the ground.

Although retaining means 26 depicted in FIGS. 2 and 3 includes only two retaining members 56 and 58, retaining means 26 could alternatively be comprised of three or more retaining members. However, regardless of the number of retaining members used to form the retaining means, none of the retaining members should extend over more than one-half of the circumference of second exterior portion 36. As is apparent, if none of the retaining members extends over more than one-half of the circumference of portion 36, then all of the retaining members can be easily placed on, and removed from, portion 36.

As indicated above, the present invention also provides a method of inserting an elongate assembly, or rod string, into the ground. In the inventive method, at least one device 20 is incorporated in the elongate assembly.

When the inventive method is used in conjunction with a cone penetrometer-type system, an elongate member 22 of a device 20 is preferably connected to the end of a rod string. A tool (e.g., a cone tip or other penetrometer-type tool) can be connected to the externally threaded portion 32 of elongate member 22 before or after elongate member 22 is connected to the rod string. Any electrical lead wires associated with the tool are threaded through passageway 28 of elongate member 22 and then through the rod string.

After elongate member 22 and the tool connected thereto have been attached to the end of the rod string, the tool and elongate member 22 are conducted through the cone penetrometer-type system (e.g., through the guiding sleeve, rod decontamination system, and/or equipment positioned within or near the floor of a cone penetrometer truck). After elongate member 22 travels through the cone penetrometer-type system but before member 22 is inserted into the ground, sleeve members 24 and 25 are positioned on the third cylindrical exterior portion 38 of elongate member 22. With sleeve members 24 and 25 thus positioned, retaining members 56 and 58 are positioned on the second cylindrical exterior portion 36 of elongate member 22. A nylon tie, a wire, or other tying means is then positioned in groove 64 of retaining means 26 to ensure that sleeve members 24 and 25 and retaining members 56 and 58 are retained on elongate member 22 in the positions shown in FIGS. 2 and 3. With friction reducing sleeve 23 and retaining means 26 thus positioned on elongate member 22, the rod string is driven into the ground.

As the rod string is driven into the ground, additional friction reducing devices 20 can be incorporated in the rod string at any desired locations. An additional device 20 is incorporated in the rod string by simply: (a) incorporating an elongate member 22 in the rod string using threaded portions 30 and 32; (b) delivering the elongate member 22 through the cone penetrometer-type system; and (c) before the elongate member 22 is driven into the ground, positioning friction reducing sleeve members 24 and 25, retaining members 56 and 58, and a tying means on elongate member 22 in the same manner as described above.

After the rod string has been used to accomplish its intended purpose, the rod string is pulled from the ground. As each device 20 reaches the surface, the device's tying means, retaining members 56 and 58, and friction reducing sleeve members 23 and 25 are removed before the device is pulled through the penetrometer-type system. All of the remaining portions of the rod string, including the penetrometer tool and all elongate members 22, are pulled through the penetrometer-type system.

In order to prevent shoulder 35 and V-shaped groove 42 of elongate member(s) 22 from damaging portions of the cone penetrometer-type system (e.g., the guiding sleeve of a penetrometer truck and/or the seals of a rod decontamination system) as the elongate member(s) is (are) pushed and pulled through the system, a damage prevention means is preferably employed. The damage prevention means is added to each elongate member 22 before the elongate member is pushed through the cone penetrometer-type system. After the elongate member is delivered through the penetrometer-type system and before the elongate member is driven into the ground, the damage prevention means is removed from the elongate member so that friction reducing sleeve members 24 and 25 and retaining members 56 and 58 can be added to the elongate member. As each elongate member is subsequently pulled from the ground, the damage prevention means is again added to the elongate member after sleeve members 24 and 25 and retaining members 56 and 58 are removed and before the elongate member is pulled through the cone penetrometer-type system.

Figure 9:
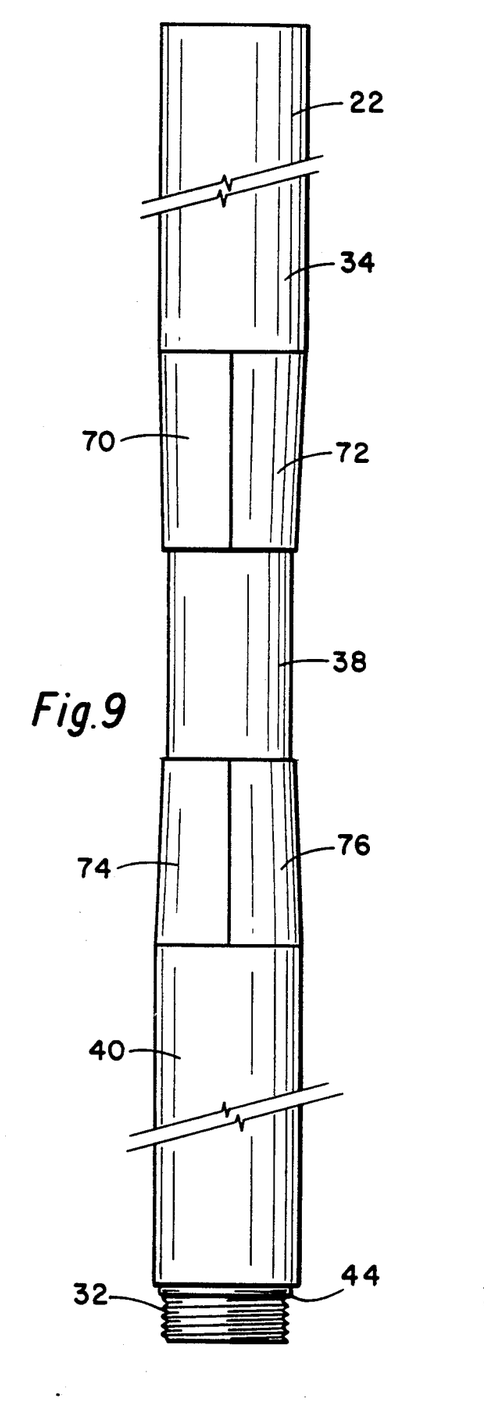
FIG. 9 provides an elevational side view of elongate member 22 having damage prevention means positioned thereon.
Figure 10:
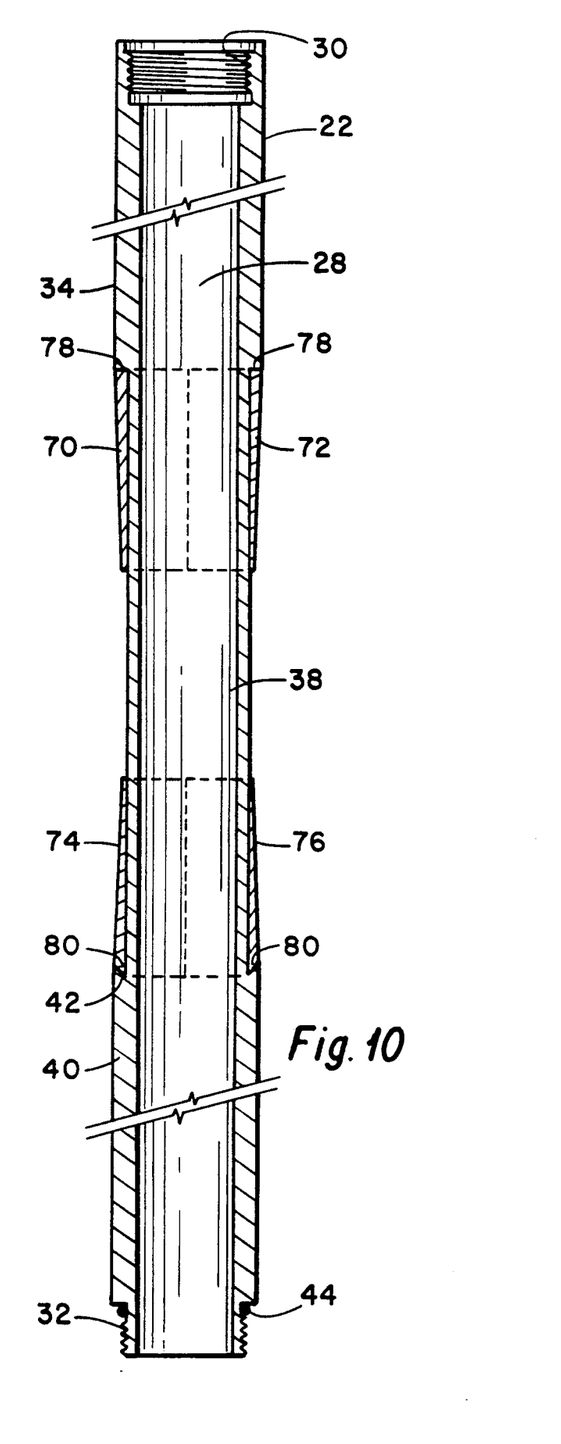
FIG. 10 provides a cutaway elevational side view of elongate member 22 having damage prevention means positioned thereon.

An embodiment of an inventive damage prevention means is depicted in FIGS. 9 and 10. The damage prevention means depicted in FIGS. 9 and 10 comprises two upper tapered members 70 and 72 and two lower tapered members 74 and 76. As shown, each tapered member 70, 72, 74, and 76 is positionable on the small diameter exterior portion 36, 38 of elongate member 22 and extends over not more than about one-half of the circumference of said small diameter exterior portion. Each of upper tapered members 70 and 72 has a flat end 78 for abutting shoulder 35 of elongate member 22. Each of lower tapered members 74 and 76 has a V-shaped end 80 which is receivable in V-shaped groove 42 of elongate member 22. After tapered members 70, 72, 74, and 76 are positioned on elongate member 22 as shown in FIGS. 9 and 10, tapered members 70, 72, 74, and 76 are taped to the small diameter exterior portion of elongate member 22 extending between the upper tapered members 70, 72 and the lower tapered members 74, 76. The application of tape to members 70, 72, 74, and 76 and to elongate member 22 serves to hold members 70, 72, 74, and 76 in position on elongate member 22 as elongate member 22 is pushed or pulled through the cone penetrometer-type system.

Thus, the present invention is well adapted to carry out the objects and obtain the ends and advantages mentioned above as well as those inherent therein. While numerous changes may be made by those skilled in the art, such changes are encompassed within the scope of the invention as defined by the appended claims.

We claim:

1. A device comprising:

a cone penetrometer system including;

an elongate member, having a first end adapted to have a driving member connected thereto and a second end adapted to have a tool connected thereto and;

means for reducing surface contact between said elongate member and the ground when said elongate member is driven into the ground, wherein said means for reducing surface contact is a friction reducing sleeve, having parallel interior surfaces, removably positionable on a first longitudinal segment of said elongate member.

2. A device as described in claim 1 wherein said sleeve comprises at least two sleeve members and wherein, when said sleeve members are positioned on said first longitudinal segment, none of said sleeve members extends around the entire circumference of said first longitudinal segment.

3. A device as described in claim 2 wherein, when all of said individual sleeve members are positioned on said first longitudinal segment, said sleeve extends around substantially the entire circumference of said first longitudinal segment.

4. A device as described in claim 2 further comprising a retaining means for retaining said sleeve on said first longitudinal segment of said elongate member.

5. A device as described in claim 4 wherein said retaining means comprises at least two retaining members removably positionable on said elongate member adjacent said sleeve and wherein, when said retaining members are positioned on said elongate member adjacent said sleeve, none of said retaining members extends around the entire circumference of said elongate member.

6. A device as described in claim 5 wherein, when all of said retaining members are positioned on said elongate member adjacent said sleeve, said retaining means extends around substantially the entire circumference of said elongate member.

7. A device as described in claim 2 wherein said first longitudinal segment of said elongate member is cylindrically-shaped.

8. A device as described in claim 7 wherein, when said sleeve members are positioned on said first longitudinal segment, none of said sleeve members extends over more than one-half of the circumference of said first longitudinal segment.

9. A device as described in claim 7 wherein each of said sleeve members has a semi-cylindrical interior surface which is positionable against said first longitudinal segment.

10. A device as described in claim 7 wherein:

said elongate member further comprises a second longitudinal segment adjacent said first longitudinal segment;

said second longitudinal segment is cylindrically-shaped; and the outside diameter of said first longitudinal segment is less than the outside diameter of said second longitudinal segment.

11. A device as described in claim 10 wherein, when said sleeve members are positioned on said first longitudinal segment, the largest outside diameter of said sleeve is greater than the outside diameter of said second longitudinal segment.

12. A device as described in claim 10 wherein each of said sleeve members has a first end and wherein the transition from said first longitudinal segment to said second longitudinal segment defines a groove for receiving said first ends of said sleeve members.

13. A device comprising:
a cone penetrometer system including;
an elongate member, having a first end adapted to have a driving member connected thereto and a second end adapted to have a tool connected thereto, said elongate member having a first, cylindrically-shaped, longitudinal segment and;
means for reducing surface contact between said elongate member and the ground when said elongate member is driven into the ground, wherein said means for reducing surface contact is a friction reducing sleeve removably positionable on a first longitudinal segment of said elongate member.

14. A device as described in claim 13 further comprising means for incorporating said elongate member into an elongate assembly.

15. A device as described in claim 13 wherein said sleeve comprises at least two sleeve members removably positionable on said first longitudinal segment and wherein, when said sleeve members are positioned on said first longitudinal segment, none of said sleeve members extends around the entire circumference of said first longitudinal segment.

16. A device as described in claim 15 wherein, when said sleeve members are positioned on said first longitudinal segment, none of said sleeve members extends over more than one-half of the circumference of said first longitudinal segment.

17. A device as described in claim 15 wherein each of said sleeve members has a semi-cylindrical interior surface which is positionable against said first longitudinal segment.

18. A device as described in claim 15 wherein:
said elongate member further comprises a second, cylindrically-shaped, longitudinal segment adjacent one end of said first longitudinal segment and
the outside diameter of said first longitudinal segment is less than the outside diameter of said second longitudinal segment.

19. A device as described in claim 18 wherein, when said sleeve members are positioned on said first longitudinal segment, the largest outside diameter of said sleeve is greater than the outside diameter of said second longitudinal segment.

20. A device as described in claim 18 wherein each of said sleeve members has a first end and wherein the transition from said first longitudinal segment to said second longitudinal segment defines a groove for receiving said first ends of said sleeve members.

21. A device as described in claim 18 further comprising a retaining means for retaining said sleeve members on said first longitudinal segment.

22. A device as described in claim 21 wherein:
said elongate member further comprises a third, cylindrically-shaped, longitudinal segment adjacent the other end of said first longitudinal segment;
said elongate member further comprises a fourth, cylindrically-shaped, longitudinal segment adjacent said third longitudinal segment; and
the outside diameter of said third longitudinal segment is less than the outside diameter of said fourth longitudinal segment.

23. A device as described in claim 22 wherein said retaining means is removably positionable on said third longitudinal segment.

24. A device as described in claim 23 wherein said retaining means comprises at least two retaining members removably positionable on said third longitudinal segment and wherein, when said retaining members are positioned on said third longitudinal segment, none of said retaining members extends around the entire circumference of said third longitudinal segment.

25. A device as described in claim 24 wherein, when said retaining members are positioned on said third longitudinal segment, none of said retaining members extends over more than one-half of the circumference of said third longitudinal segment.

26. A device as described in claim 25 wherein said elongate member has a passageway extending longitudinally therethrough.

27. A method of inserting a device into the earth comprising: providing a cone penetrometer system having an elongate assembly; incorporating a friction reducing device in said elongate assembly, said friction reducing device comprising:
an elongate member having a first, cylindrically-shaped, longitudinal segment;
a friction reducing sleeve removably positioned on said first longitudinal segment; and
means for incorporating said elongate member in said elongate assembly;
and driving said elongate assembly into the earth such that the friction reducing device minimizes contact between the ground and the elongate assembly.

28. A method as described in claim 27 wherein:
said elongate member further comprises a second, cylindrically-shaped longitudinal segment adjacent one end of said first longitudinal segment and
the outside diameter of said first longitudinal segment is less than the outside diameter of said second longitudinal segment.

29. A method as described in claim 28 wherein said sleeve comprises at least two sleeve members removably positioned on said first longitudinal segment and wherein, when said sleeve members are positioned on said first longitudinal segment, none of said sleeve members extends around the entire circumference of said first longitudinal segment.

30. A method as described in claim 29 wherein said friction reducing device further comprises a retaining means for retaining said sleeve members on said first longitudinal segment.

31. A method as described in claim 28 wherein said elongate member has a passageway extending longitudinally therethrough.

32. A method as described in claim 28 wherein said step of incorporating includes the steps of:
(a) incorporating said elongate member in said elongate assembly and
(b) positioning said sleeve on said first longitudinal segment of said elongate member.

33. A method as described in claim 32 wherein, after step (a) and prior to step (b), said method further comprises the step of conducting said elongate member through said cone penetrometer-type system.

34. A method as described in claim 33 further comprising the step, after step (a) and prior to said step of conducting, of positioning a damage prevention means on said elongate member for preventing said elongate member from damaging said cone penetrometer-type system.

35. A method as described in claim 34 further comprising the step, after said step of conducting and prior to step (b), of removing said damage prevention means from said elongate member.

36. A method as described in claim 33 further comprising the steps, after step (c), of:
   (d) pulling said elongate member out of the ground;
   (e) removing said sleeve from said elongate member; and then
   (f) conducting said elongate member through said cone penetrometer-type system.

37. A method as described in claim 36 further comprising the step, after step (e) and prior to step (f), of positioning a damage prevention means on said elongate member for preventing said elongate member from damaging said cone penetrometer-type system.

* * * * *